United States Patent [19]

Doner et al.

[11] Patent Number: 4,743,386
[45] Date of Patent: * May 10, 1988

[54] GREASE COMPOSITIONS CONTAINING PHENOLIC- OR THIO-AMINE BORATES AND HYDROXY-CONTAINING SOAP THICKENERS

[75] Inventors: John P. Doner, Sewell; Andrew G. Horodysky, Cherry Hill; John A. Keller, Jr., Pitman, all of N.J.

[73] Assignee: Mobil Oil Corporation, New York, N.Y.

[*] Notice: The portion of the term of this patent subsequent to Dec. 4, 2001 has been disclaimed.

[21] Appl. No.: 769,826

[22] Filed: Aug. 27, 1985

Related U.S. Application Data

[60] Continuation-in-part of Ser. No. 682,579, Dec. 17, 1984, abandoned, which is a continuation of Ser. No. 445,883, Dec. 1, 1982, abandoned, which is a continuation-in-part of Ser. No. 638,609, Aug. 7, 1984, Pat. No. 4,571,248, which is a division of Ser. No. 456,880, Jan. 10, 1983, Pat. No. 4,486,321.

[51] Int. Cl.$^4$ .......................................... C10M 139/00
[52] U.S. Cl. .............................. 252/49.6; 252/32.7 E; 252/47; 252/47.5
[58] Field of Search .................... 252/49.6, 32.7 E

[56] References Cited

U.S. PATENT DOCUMENTS

| | | | |
|---|---|---|---|
| 2,053,474 | 9/1936 | Graves et al. | 260/98 |
| 2,397,956 | 4/1946 | Fraser | 252/40 |
| 2,703,784 | 3/1955 | Fields | 252/32.7 |
| 2,703,785 | 3/1955 | Roberts et al. | 252/33.4 |
| 2,813,830 | 11/1957 | Trautman | 252/49.6 |
| 3,009,791 | 11/1961 | Emrick | 44/63 |
| 3,012,968 | 12/1961 | Emrick et al. | 252/49.6 |
| 3,697,574 | 10/1972 | Piasek et al. | 252/49.6 |
| 3,704,308 | 11/1972 | Piasek et al. | 252/49.6 |
| 3,736,357 | 5/1973 | Piasek et al. | 252/49.6 |
| 3,751,365 | 8/1973 | Piasek et al. | 252/49.6 |
| 4,016,092 | 4/1977 | Andress | 252/49.6 |
| 4,140,492 | 2/1979 | Feldman et al. | 44/62 |
| 4,159,957 | 7/1979 | de Vries | 252/49.6 |
| 4,317,739 | 3/1982 | Spence | 252/47.5 |
| 4,376,712 | 3/1983 | Horodysky et al. | 252/49.6 |
| 4,382,006 | 5/1983 | Horodysky | 252/49.6 |
| 4,394,278 | 7/1983 | Horodysky et al. | 252/46.3 |
| 4,426,305 | 1/1984 | Malec | 252/49.6 |
| 4,440,656 | 4/1984 | Horodysky | 252/49.6 |
| 4,486,321 | 12/1984 | Horodysky et al. | 252/46.3 |
| 4,524,005 | 6/1985 | Horodysky | 252/49.6 |
| 4,529,529 | 7/1985 | Horodysky | 252/49.6 |
| 4,582,617 | 4/1986 | Doner et al. | 252/32.7 |

OTHER PUBLICATIONS

C. J. Boner, "Manufacture and Application of Lubricating Greases", 1954, pp. 435–437, 497–498, 157.
C. V. Smalheer & R. K. Smith, "Lubricant Additives", 1967, Section 1, pp. 1–11, Chapter 1.
G. G. Hawley, "The Condensed Chemical Dictionary", Ninth Edition, pp. 520 and 938.

*Primary Examiner*—William R. Dixon, Jr.
*Assistant Examiner*—Ellen McAvoy
*Attorney, Agent, or Firm*—Alexander J. McKillop; Michael G. Gilman; Van D. Harrison, Jr.

[57] ABSTRACT

The dropping point temperature of a grease containing a hydroxy-bearing thickener is increased by including in the grease composition a borated or boron containing phenolic or thio amine Mannich base. A sulfur-phosphate compound, zinc dithiophosphate can also be added to further improve the dropping point.

29 Claims, No Drawings

GREASE COMPOSITIONS CONTAINING PHENOLIC- OR THIO-AMINE BORATES AND HYDROXY-CONTAINING SOAP THICKENERS

CROSS-REFERENCE TO RELATED APPLICATIONS

This application is a continuation-in-part of copending U.S. application Ser. No. 682,579, filed Dec. 17, 1984, now abandoned, which is a continuation of U.S. application Ser. No. 445,883, filed Dec. 1, 1982, now abandoned. The present application is also a continuation-in-part of copending U.S. application Ser. No. 638,609, filed Aug. 7, 1984, now U.S. Pat. No. 4,571,248, which is a division of U.S. application Ser. No. 456,880, filed Jan. 10, 1983, now U.S. Pat. No. 4,486,321. U.S. Pat. No. 4,486,321 and application Ser. No. 682,579 (12/17/84) are incorporated herein by reference.

BACKGROUND OF THE INVENTION

1. Nature of the Invention

The invention is concerned with grease compositions. More particularly it is concerned with a grease composition comprising oil, hydroxy-containing soap thickener and certain borated phenolic- or thio-amine Mannich bases and, optionally, phosphorus and sulfur moieties.

2. Prior Art

The publication "Manufacture and Application of Lubricating Grease by C. J. Boner (Reinhold Publishing Company) 1954, pp. 155 and 436, 437 disclose the use of lithium soaps in grease making. The publication "Lubricant Additive" by C. V. Smalheer et al (Leyuis-Hiles Co.) 1967, pp. 1–11, discloses the use of phosphonates and thiophosphonates as additives in lubricants. "Condensed Chemical Dictionary" 9th Edition, (Van Nostrand Reinhold Company) at pages 520 and 938 discloses the use of lithium hydroxystearate in grease making and zinc dialkyldithiophosphate as a lube oil additive.

These references, the publications by Boner and by Smalheer et al, and the "Condensed Chemical Dictionary" reference are incorporated herein by reference.

SUMMARY OF THE INVENTION

In accordance with this invention, there is provided an improved grease composition comprising a major proportion of a grease, a hydroxy-containing soap thickener and a minor amount of a boronated phenolic- or thio-amine Mannich base. The hydroxy-containing soap thickener and phenolic- or thio-amine compound are each added in amounts sufficient to increase the dropping point of the grease an appreciable amount useful in this invention. This is generally an increase of at least 15° F. but can be as great as 200° to 250° F. or more.

The Borated Mercaptan Amine Aldehyde Products

The mercaptan amine aldehyde compounds that are borated for use in this invention are prepared as described in U.S. Pat. No. 4,486,321 and are mixtures of compounds, some of which have the following possible structures:

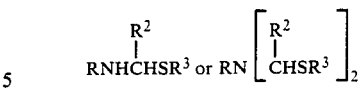

wherein R is H or a $C_1$ to $C_{20}$ hydrocarbyl group, $R^1$ is a $C_2$ to $C_5$ alkylene group, $R^2$ is H or a $C_1$ to $C_8$ hydrocarbyl group (e.g., alkyl, alkenyl, cycloalkyl, alkaryl or aralkyl and $R^3$ is a $C_8$ to $C_{30}$ hydrocarbyl group, preferably an alkyl group. $R^3$ can be a straight chain or branched chain, with the straight chain being preferred.

These mercaptan amine aldehyde compounds are borated with any appropriate boron-containing compound. Preferred, because of ease of reaction are boric oxide or a boron compound of the formula

where $R^4$ is a $C_1$ to $C_6$ alkyl, a is 0 to 3 and b is 0 to 3, the sum of a and b being 3.

Additional details are disclosed in the incorporated U.S. Pat. No. 4,486,321.

The Borated Mannich Base (Phenol-Amine) Reaction Products

Borated Mannich base reaction products are disclosed in pending U.S. application Ser. No. 682,579, filed Dec. 17, 1984, which is a continuation of Ser. No. 445,883, filed Dec. 1, 1982. This application (Ser. No. 682,579) is incorporated herein by reference.

The borated Mannich base reaction product described in application Ser. No. 628,579 is made by borating a product made by reacting an aldehyde, an amine and one or more phenols of the formula:

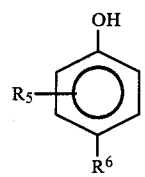

wherein $R_5$ is preferably hydrogen, but can be a $C_1$ to $C_{30}$ hydrocarbyl group, which may be an alkyl, alkenyl, aryl, alkaryl or aralkyl group. $R^6$ is a hydrocarbyl group, preferably alkyl or alkenyl containing 4 to 20 carbon atoms, and can additionally contain sulfur, oxygen and/or nitrogen atoms. $R^6$ can also be a polymeric group having a molecular weight up to between 1000 and 2000 and can be polypropyl, polybutenyl, polyisobutyl or the like. The lower molecular weights of 4 to 20 carbon atoms are, however, preferred. The groups more preferable are tertiary hydrocarbyl groups which provide increased stability and activity. In $R_5$, the aryl group can be one having from 6 to 14 carbon atoms, i.e. phenyl, naphthyl or anthryl.

In carrying out the reaction to form the Mannich base, the phenol:aldehyde:amine molar ratios used can be 1:0.1–10:0.1–10 or broader, respectively.

Representative phenols that can be used are p-tert-butylphenol, p-tert-octylphenol, p-tert-dodecylphenol, p-tert-hexadecylphenol, dodecyl phenol, nonyl phenol and the like.

Aldehydes that can be used are the aliphatic aldehydes, typified by formaldehyde or paraformaldehyde, acetaldehyde, and aldol(-hydroxy butyraldehyde); aromatic aldehydes, such as benzaldehyde and heterocyclic aldehydes, such as furfural. The aldehyde may contain a substituent group such as hydroxyl, halogen, nitro and the like. In short, any substituent can be used which does not take a major part in the reaction. Preference, however, is given to the aliphatic aldehydes, formaldehyde being particularly preferred.

The amines to be used include those which contain a primary amino group. Preferably, these include saturated and unsaturated aliphatic amines containing 1 to 20 carbon atoms. They more specifically include those of the structural formula:

$$R^7NH_2$$

wherein $R^7$ is a hydrocarbyl group having from 4 to 20 carbon atoms. These are preferably $C_6$ to $C_{18}$ straight or branched alkyl groups, but may be cyclic, the latter of which include cyclohexylamine. Straight chain amines are more preferred and include cocoamine, oleylamine, octylamine, nonylamine, decylamine, dodecylamine, tetradecylamine, hexadecylamine, octadecylamine, cyclooctylamine, laurylamine, isostearylamine, and soyamine. Polyethylene amines can be used such as ethylenediamine, diethylenetriamine, triethylenetetraamine, tetraethylenepentamine, corresponding propylenediamines and similar amines.

Other amines which can be used include:

(a) etheramines (hydrocarbyloxy hydrocarbyl amines) such as tri isodecyloxypropyl amine and etheramines of the formula $R^7OR^9NH_2$ where $R^7$ is as stated above and $R^9$ is a $C_1$ to $C_6$ hydrocarbyl group;

(b) N-hydrocarbyl hydrocarbylene diamines or triamines such as N-oleyl-1,3 propylene or N-coco-1,2-ethylenediamine or amines of the structure

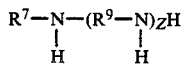

where $R^7$ and $R^9$ are as indicated above and Z is 1 to 3;

(c) etherdiamines (hydrocarbyloxy hydrocarbyl hydrocarbyl diamines) such as those of the structure

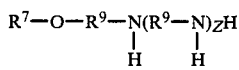

where $R^7$ and $R^9$ are as indicated above and Z is 1 to 3;

Also useful are aryl-hydrocarbylene amines and diamines.

The phenols used in this invention can be and have been purchased from commercial sources. In general, if desired or necessary, they can be prepared by reactions generally known to the art, such as alkylation reactions of phenol.

The borating agent can be any appropriate boron compound, including, but not limited to, boric acid, metaborates, boric oxide or a compound of the formula:

$$(R^8O)_xB(OH)_y$$

wherein $R^8$ is a $C_1$ to $C_6$ alkyl group, x is 0 to 3 and y is 0 to 3, their sum being 3. As indicated by the formula, included are boric acid and the alkyl borates, such as the mono-, di- and trialkyl borates.

The reactions between phenol, amine and aldehyde, and between the Mannich base obtained and the boronation agent are carried out at from about 80° C. to about 150° C. and from about 80° C. to about 260° C., preferably about 110° C. to about 180° C., respectively.

The temperature chosen will depend for the most part on the particular reactants and on whether or not a solvent is used. In carrying out the boronation reaction, it is preferable that quantities of reactants be chosen such that the molar ratio of Mannich bases to boron compound be from about 0.2 to 1 to about 3 to 1, preferably from about 0.5 to 1 to about 2 to 1. The Mannich base can be partially borated, or reacted with an excess of the borating species to form a composition containing from about 0.1% by weight of boron to as much as 10% boron or more. An excess of boronating agent of up to 100 percent can be used. On occasion an excess of up to 1000 percent may be desirable.

While atmospheric pressure is generally preferred, either reaction can be advantageously run at from about 1 to about 0.5 atmospheres. Furthermore, where conditions warrant it, a solvent may be used. In general, any relatively non-polar, unreactive solvent can be used, including benzene, toluene, xylene and 1,4-dioxane. Other hydrocarbon and alcoholic solvents, the latter which include propanol, butanol and the like, can be used. Further, mixtures of hydrocarbons, and for example, alcohols may be advantageous.

While the preferred mode of synthesis of the Mannich base involves a one-step reaction in which all reactants are placed together, other modes can be used. For example, phenol and amine can be reacted to yield an ammonium phenate, and this product is then reacted with an aldehyde. This mode is not favorable, since one tends to get methylene bridged polymers. A third possible scheme involves the reaction of amine and aldehyde to yield a Schiff base (RN=CH$_2$), followed by reaction of the Schiff base with phenol to give the product. Results using this reaction are more favorable than the second scheme mentioned, and they appear to be similar to the first reaction.

Reaction times are not critical, and can range from about 1 hour or less up to 8 hours or more, depending, among other things, upon the particular reactants and the solvent used.

The additives of the invention have been disclosed to be reaction products, not identifiable single compounds. While they are believed to be complex mixtures of all the possible products obtainable from any given reaction mixture, the products are believed to contain substantial or even predominant amounts of compounds II and III as shown in the following illustrative reactions when phenols, aldehydes and hydrocarbylated phenols are used as reactants:

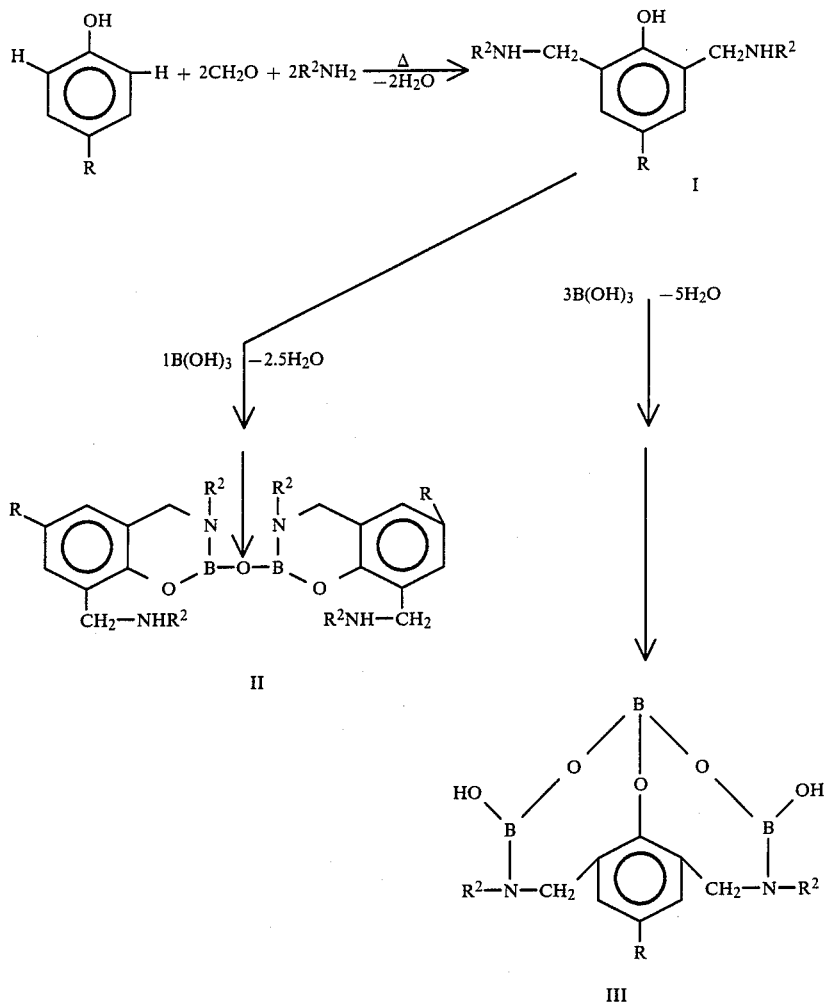

R = tert-butyl (generally, branched $C_3$-$C_{12}$)
$R^2$ = coco($C_8$-$C_{18}$)

A narrow class of thickening agents is used to make the grease of this invention. The thickening agents contain at least a portion of alkali metal, alkaline earth metal or amine soaps of hydroxyl-containing fatty acids, fatty glycerides and fatty esters including methyl esters and ethyl esters having from 12 to about 30 carbon atoms per molecule. The metals are typified by sodium, lithium, calcium and barium. Preferred is lithium. Preferred members among these acids and fatty materials are 12-hydroxystearic acid and glycerides containing 12-hydroxystearates, 14-hydroxystearic acid, 16-hydroxystearic acid and 6-hydroxystearic acid.

From 3% to 20% total thickener can be used, but the entire amount of thickener need not be derived from the aforementioned members. Significant benefit can be attained using as little thereof as about 5 to 15 percent by weight of the total thickener and up to 100 percent of the total thickener. A complementary amount, i.e., up to about 85% by weight of a wide variety of thickening agents can be used in the grease of this invention. Included among the other useful thickening agents are alkali and alkaline earth metal soaps of methyl-12-hydroxystearate, diesters of a $C_4$ to $C_{12}$ dicarboxylic acid and tall oil fatty acids. Other alkali or alkaline earth metal fatty acids containing from 12 to 30 carbon atoms and no free hydroxyl may be used. These include soaps of stearic and oleic acids.

Greases benefiting from the borated additive can be produced by any of the commonly used manufacturing techniques which include open or closed kettle saponification. Saponification can also be carried out in pressure vessels commonly known as contactors, at a variety of temperatures and pressures. Continuous grease production equipment can also be used to produce the grease which will be treated with the borated additive. Operating temperatures and pressures are variable depending on the type of reactants involved. Temperatures generally range from room temperature 25° C. to 232° C. and pressures range from as high as 190 psig to as low as vacuum.

Other thickening agents include salt and salt-soap complexes as calcium stearate-acetate (U.S. Pat. No. 2,197,263), barium stearate acetate (U.S. Pat. No. 2,564,561), calcium, stearate-caprylate-acetate complexes (U.S. Pat. No. 2,999,065), calcium caprylate-acetate (U.S. Pat. No. 2,999,066), and calcium salts and soaps of low-, intermediate- and high-molecular weight acids and of nut oil acids.

Another group of thickening agents comprises substituted ureas, phthalocyanines, indanthrene, pigments such as perylimides, pyromellitdiimides, and ammeline, as well as certain hydrophobic clays. These thickening agents can be prepared from clays which are initially hydrophilic in character, but which have been converted into a hydrophobic condition by the introduction of long-chain hydrocarbon radicals into the surface of the clay particles prior to their use as a component of a grease composition, as, for example, by being subjected to a preliminary treatment with an organic cationic surface active agent, such as an onium compound. Typical onium compounds are tetraalkylammonium chlorides, such as dimethyl dioctadecyl ammonium chloride, dimethyl dibenzyl ammonium chloride and mixtures thereof. These methods of manufacture, being well known to those skilled in the art, are believed to require no further discussion, and do not form a part of the present invention.

The third member(s) that may be present in the grease composition are the phosphorus and sulfur moieties. Both of these can be present in the same molecule, such as in a metal or non-metal phosphorodithioate of the formula

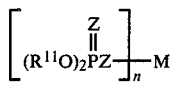

wherein $R^{11}$ is a hydrocarbyl group containing 3 to 18 carbon atoms. $R^{11}$ can also be hydroxyl-containing or ester-containing hydrocarbyl groups and additionally can contain sulfur. M is preferably a metal, but may be a non-metal, such as one of those mentioned hereinbelow; n is the valence of M and Z is oxygen or sulfur, at least one Z being sulfur.

In this compound, $R^{11}$ is preferably an alkyl group and may be a propyl, butyl, pentyl, hexyl, octyl, decyl, dodecyl, tetradecyl or octadecyl group, including those derived from isopropanol, propanol, butanol, isobutanol, sec-butanol, 4-methyl-2-pentanol, 2-ethylhexanol, oleyl alcohol, and mixtures thereof. Further included are alkaryl groups such as butylphenol, octylphenyl, nonylphenyl and dodecylphenyl groups.

The phosphorodithioate can also be derived from diols such as 1,2-decanediol or 1,3-pentanediol or similar diols or can be derived from hydroxy esters.

The metals embraced by M include those in Groups IA, IIA, IIB, and VIII of the Periodic Table. Some that may be mentioned are lithium, sodium, calcium, zinc, cadmium, silver, gold and molybdenum. Non-metallic ions include organic groups derived from vinyl esters such as vinyl acetate, vinyl ethers such as butyl vinyl ether and epoxides such as propylene oxide and 1,2-epoxydodecane. The non-metallic ions may also be derived from nitrogenous compounds such as those derived from hydrocarbyl amines and diamines, including oleylamine and N-oleyl-1,3-propylenediamine and such as the imidazolines and oxazolines.

The phosphorodithioate can also be complexed, as for example, a zinc acetate complexed zinc phosphorodithioate.

The phosphorus and sulfur can also be supplied from the combination of two separate compounds, such as the combination of (1) a dihydrocarbyl phosphite having 2 to 10 carbon atoms in each hydrocarbyl group or mixtures of phosphites and (2) a sulfide such as sulfurized isobutylene, dibenzyl disulfide, sulfurized terpenes, phosphorodithionyl disulfide and sulfurized jojoba oil. The phosphites include the dibutyl, dihexyl, dioctyl, didecyl and similar phosphites. Phosphate esters containing 4 to 20 carbon atoms in each hydrocarbyl group, such as tributyl phosphate, tridecyl phosphate, tricresyl phosphate and mixtures of such phosphates, can also be used. Compounds containing both sulfur and phosphorus such as phosphorodithionyl disulfide can be used. Related compounds and mixtures thereof can also be used.

In summary, it is essential to the practice of this invention, in which greases having improved dropping points are obtained, that at least the borated phenolic- or thio-amine compounds and the hydroxy-containing thickener be included in the grease composition. Thus:

first, with respect to the preparation of the grease, the thickener will have at least about 15% by weight of a metal or non-metal hydroxyl-containing soap therein, the total thickener being from about 3 percent to about 20 percent by weight of the grease composition;

second, there will be added to the grease from about 0.1 percent to about 10.0 percent by weight, preferably about 0.5 percent to about 2.0 percent of a borated phenolic- or thio-amine compound or mixture of such compounds, and as a third component optionally, the composition may have therein from 0.2 percent to about 10.0 percent by weight, preferably from 1.0 percent to 2.0 percent by weight, of phosphorus- and sulfur-containing compounds or a mixture of two or more compounds which separately supply the phosphorus and sulfur moieties. If separate compounds are used, an amount of the mixture equivalent to the above concentration levels is used to supply desired amounts of phosphorus and sulfur.

Base oils used in the grease are mineral oils, synthetics, hydrocarbon liquids or mixtures of these hydrocarbon liquids. In addition, oxygen containing fluids can be used such as dibasic acid esters, polyol esters, polyglycols, or phosphate esters. The alkyl benzene type lubricants are also included. Other fluids that may be used are halogenated fluids, silicones, silicate esters, or polyphenyl ethers. These lubricant fluids can be mixed or used alone as the base oil portion of the grease.

In general, mineral oils, both paraffinic naphthenic and mixtures thereof, may be of any suitable lubricating viscosity range, as for example, from about 45 SSU at 100° F. to about 6000 SSU at 38° C. (100° F.), and preferably from about 50 to about 250 SSU at 94° C. (210° F.). These oils may have viscosity indexes ranging to about 100 or higher. Viscosity indexes from about 70 to about 95 are preferred. The average molecular weights of these oils may range from about 250 to about 800. In making the grease, the lubricating oil from which it is prepared is generally employed in an amount sufficient to balance the total grease composition, after accounting for the desired quantity of the thickening agent, and other additive components to be included in the grease formulation.

In instances where synthetic oils are desired, in preference to mineral oils, various compounds of this type may be successfully utilized. Typical synthetic vehicles include polyisobutylene, polybutenes, hydrogenated polydecenes, polypropylene glycol, polyethylene glycol, trimethylol propane esters, neopentyl and pentaerythritol esters, di(2-ethylhexyl)sebacate, di(2-ethylhexyl)adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl)ether, phenoxy phenylethers.

The metallic soap grease compositions containing one or more of the borated friction reducing compounds and hydroxy-containing soap thickeners and, optionally, one or more of the sulfur and phosphorus combinations described herein provide advantages in increased dropping point, improved grease consistency properties, antirust characteristics and potential antifatigue, antiwear and antioxidant benefits unavailable in any of the prior greases known to us. The grease of this invention is unique in that it can be preferably manufactured by the admixture of additive quantities of the borated phenolic- or thio-amine compounds to the fully formed soap grease after completion of saponification.

EXAMPLES

EXAMPLE A

Fully Formulated Lithium Hydroxystearate Grease

This example illustrates the preparation of a grease containing a hydroxy-bearing thickener and a phosphorus-sulfur compound, but lacking the borated compound. This grease approximates a prior art or state of the art grease.

A lithium hydroxystearate grease thickener was prepared by a saponifying mixture containing 50 weight percent of 12-hydroxystearic acid in a mixture of the acid and the glycerine thereof with lithium hydroxide in a mineral oil vehicle at about 177° C. (351° F.) in a closed contactor. After the thickener had been depressured and dehydrated in an open kettle, sufficient mineral oil was added to reduce the thickener content to about 9.0%. After the grease had cooled to 99° C., a typical grease additive package, consisting of an amine antioxidant, phenolic antioxidant, metallic dithiophosphate (phosphorodithioate), sulfur-containing metal deactivator and nitrogen containing antitrust additives, was added. This produced a fully formulated hydroxyl-containing soap grease. The dropping point of this formulated grease was 202° C. (395° F.). The grease was tested for dropping point to compare it with greases formulated according to this invention.

EXAMPLE B

Lithium Hydroxystearate Base Grease

This example illustrates the preparation of a grease containing a hydroxy-bearing thickener but without any additive package of sulfur and phosphorus compounds. This grease approximates a prior art grease without additives.

A lithium hydroxystearate-thickened base grease was prepared as generally described for Example A. No additive package was added to the grease. After reduction of the thickener content to about 10%, the grease (without additives) was cooled and held for subsequent testing. The dropping point of this base grease was 202° C. (395° F.).

EXAMPLE C

Lithium Stearate/Palmitate-Thickened Base Grease

A lithium stearate/palmitate (50% stearate/50% palmitate) base grease not containing any hydroxyl groups in the soap thickeners was prepared for evaluation as generally described in Example B. The total thickener content was about 10%. The dropping point was 207° C. (405° F.).

The effect of blending in two percent of each of the boron compounds described above into the hydroxystearate thickened grease and into the nonhydroxyl-containing stearate/palmitate-thickened grease was tested by measuring the dropping point of the mixed greases. Other blends of the greases were also tested. The test data is summarized in the accompanying table. It will be noted that the combination of hydroxyl bearing thickener and borated phenolic amine compound results in a grease of greatly improved dropping point. The further addition of sulfur and phosphorus compounds acted also to increase the dropping point.

Example I

Preparation of Phenolic Amine Borate

Approximately 600 grams of p-t-butylphenol, 252 grams of paraformaldehyde, 1680 grams of cocoamine, and 500 grams of toluene were placed in a reactor equipped with heater, agitator, and Dean-Stark tube with condenser. The reactor contents were heated to 135° C. (275° F.) over a period of 11 hours during which time water evolution during azeotropic distillation ceased. The toluene solvent was removed by distillation under reduced pressure at 135° C. (275° F.) and the intermediate was filtered through diatomaceous earth to form:

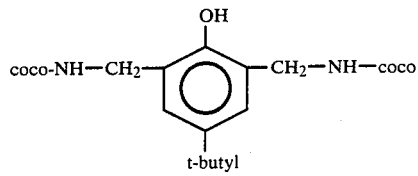

Approximately 119 grams of the above Mannich base condensation product, 150 grams of diluent oil, 100 grams of toluene, and 61.8 grams of boric acid were charged to a reactor equipped as described above. The temperature was raised to 172° C. (342° F.) over a period of 6 hours until no more water evolved. The solvent was removed by distillation at 170° C. (342° F.) under reduced pressure and the product was filtered hot through diatomaceous earth.

TABLE

| Grease Composition | Borated Compound | % of Borated Compound in Composition | % of Zinc Dialkyl Thiophosphate | Dropping Point, ASTM D 2265 |
|---|---|---|---|---|
| Example A - Hydroxy-bearing thickener & phosphorus-sulfur compound | | 0 | 1.5 | 202° C. (395° F.) |
| Example B - Hydroxy-bearing thickener. No added phosphorus or sulfur or other additives | | 0 | 0 | 202° C. (395° F.) |
| Example C - Lithium stearate/palmitate thickener. No hydroxy-bearing thickener or added sulfur or phosphorus compounds | | 0 | 0 | 207° C. (405° F.) |
| Example B-1 | phenolic amine borate | 2% | 0 | 264° C. (507° F.) |
| Example B-2 | phenolic amine borate | 2% | 1.5% | 299° C. (570° F.) |

| Grease Composition | Borated Compound | % of Borated Compound in Composition | % of Zinc Dialkyl Thiophosphate | Dropping Point, ASTM D 2265 |
|---|---|---|---|---|
| Example C-1 | phenolic amine borate | 2% | 0 | 203° C. (398° F.) |

What is claimed is:

1. A grease composition comprising a lubricating component, a thickener including at least in part a hydroxy-containing thickener, and a borated mercaptan amine aldehyde condensation product having the structural formula, before being borated,

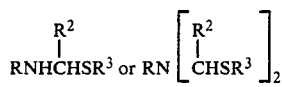

wherein R is H or a $C_1$ to $C_{20}$ hydrocarbyl group, $R^1$ is a $C_2$ to $C_5$ alkylene group, $R^2$ is H or a $C_1$ to $C_8$ hydrocarbyl group and $R^3$ is a $C_8$ to $C_{30}$ straight-chain or branched chain hydrocarbyl group, the hydroxy-containing thickener and borated mercaptan, amine aldehyde condensation product being present in sufficient quantities to effect an increase in the dropping point of said grease.

2. The composition of claim 1 wherein said borated condensation product is present in said grease composition in an amount of between about 0.2 and about 10 percent by weight.

3. The composition of claim 1 wherein the total amount of thickener added is between about 3 and about 20 percent by weight of the total composition.

4. The composition of claim 3 wherein the thickener contains at least 15 percent by weight of hydroxy-containing thickener.

5. The composition of claim 1 wherein said grease contains between about 0.2 and about 10 percent by weight of phosphorus and sulfur containing compounds.

6. The composition of claim 5 wherein said phosphorus and sulfur compound is zinc dialkyldithiophosphate or zinc diaryldithiophosphate.

7. The composition of claim 1 wherein said amine has the formula $$R^7NH_2$$

where $R^7$ is a hydrocarbyl group having 4 to 20 carbon atoms.

8. The composition of claim 7 wherein $R^7$ also contains sulfur, oxygen, or nitrogen.

9. The composition of claim 1 wherein the lubricating component is mineral oil, synthetic oil, or a mixture thereof.

10. The composition of claim 9 wherein the synthetic oils are polyglycols, synthetic hydrocarbons, alkyl benzenes, dibasic acid esters, polyol esters, phosphate esters or mixtures thereof.

11. The composition of claim 1 wherein the amine is a polyethylene amine selected from the group consisting of ethylenediamine, diethylenetriamine, triethylenetetraamine, tetraethylenepentamine, and mixtures thereof.

12. A grease composition comprising a lubricating component, a hydroxy-containing thickener and a borated condensation product obtained by reacting an amine selected from the group consisting of etheramines having the structural formula, $R^7OR^9NH_2$, amines of the structural formula

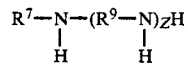

and ether diamines of the structural formula

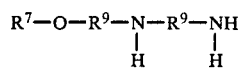

where $R^7$ is a hydrocarbyl group having from 4 to 20 carbon atoms, $R^9$ is a hydrocarbyl group of 1 to 6 carbon atoms, and Z is 1 to 4 with an aldehyde and a phenol having a substituted hydrocarbyl group of about 4 to about 20 carbon atoms or mercaptan and subsequently reacting the resulting product with a boron compound, the hydroxy-containing thickener and borated amine condensation product being present in sufficient quantities to effect an increase in the dropping point of said grease.

13. A method for elevating the dropping point of a grease composition comprising incorporating into said grease (1) the borated condensation product resulting from the reaction of a boron compound with a condensation product produced by reacting an aldehyde and an amine selected from the group consisting of etheramines having the structural formula, $R^7OR^9NH_2$, amines of the structural formula

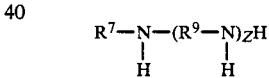

and ether diamines of the structural formula

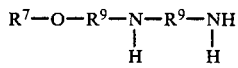

where $R^7$ is a hydrocarbyl group having from 4 to 20 carbon atoms, $R^9$ is a hydrocarbyl group of 1 to 6 carbon atoms, and Z is 1 to 4 with a mercaptan or phenol having a hydrocarbyl substituent group of about 4 to about 20 carbon atoms and (2) a thickener including at least in part a hydroxy-containing soap thickener.

14. The method of claim 13 wherein a sulfur-phosphorus containing material is also included in the grease compositions.

15. The method of claim 13 wherein the hydroxy-containing soap thickener is at least 15% by weight of the total thickener in said grease composition.

16. The method of claim 13 and adding to said grease composition one or more compounds containing sulfur and phosphorus.

17. In a method for making grease wherein a liquid lubricant is mixed with a thickening agent, the iprovement comprising adding to said grease a hydroxy-containing thickener and a borated mercaptan amine aldehyde condensation product having the structural formula before being borated of $$RNHCHSR^3 \text{ or } RN\left[\begin{array}{c} R^2 \\ | \\ CHSR^3 \end{array}\right]_2$$

wherein R is H or a $C_1$ to $C_{20}$ hydrocarbyl group, $R^1$ is a $C_2$ to $C_5$ alkylene group, $R^2$ is H or a $C_1$ to $C_8$ hydrocarbyl group and $R^3$ is a $C_8$ and $C_{30}$ straight-chain or branched chain hydrocarbyl group, the hydroxy-containing thickener and borated mercaptan, amine aldehyde condensation product being present in sufficient quantities to effect an increase in the dropping point of said grease.

18. The method of claim 12 and adding one or more compounds containing sulfur and phosphorus.

19. A grease composition comprising a lubricating component, a thickener including at least in part a hydroxy-containing thickener and the product obtained by borating the condensation product of an aldehyde, a mercaptan and an amine selected from the group consisting of etheramines having the structural formula, $R^7OR^9NH_2$, amines of the structural formula $$R^7-N-(R^9-N)_ZH \atop | \quad\quad\;\; | \atop H \quad\quad\;\; H$$

and ether diamines of the structural formula $$R^7-O-R^9-N-R^9-NH \atop \quad\quad\;\; | \quad\quad\;\; | \atop \quad\quad\;\; H \quad\quad\;\; H$$

where $R^7$ is a hydrocarbyl group having from 4 to 20 carbon atoms, $R^9$ is a hydrocarbyl group of 1 to 6 carbon atoms, and Z is 1 to 4.

20. The composition of claim 19 wherein said borated condensation product is present in said grease composition in an amount of between about 0.2 and about 10 percent by weight.

21. The composition of claim 19 wherein the total amount of thickener added is between about 3 and about 20 percent by weight of the total composition.

22. The composition of claim 21 wherein the thickener contains at least 15 percent by weight of hydroxy-containing or polyhydroxy-containing thickener.

23. The composition of claim 19 wherein said grease contains between about 0.2 and about 10 percent by weight of phosphorus and sulfur containing compounds.

24. The composition of claim 19 wherein said hydroxy-containing thickener is lithium hydroxystearate.

25. The composition of claim 23 wherein said phosphorus and sulfur compound is zinc dialkyldithiophosphate.

26. The composition of claim 19 wherein the amine is a polyethylene amine selected from the group consisting of ethylenediamine, diethylenetriamine, triethylenetetraamine, tetraethylenepentamine, and mixtures thereof.

27. A grease composition comprising a lubricating component, a thickener including at least in part a hydroxy-containing thickener and the product obtained by borating the condensation product of an aldehyde, a mercaptan and an amine of the structural formula $$RNH_2$$

where R is a hydrocarbyl group having 1 to 20 carbon atoms.

28. A grease composition comprising a lubricating component, a hydroxy-containing thickener, and a borated mercaptan polyethylene amine aldehyde condensation product wherein the polyethylene amine is selected from the group consisting of ethylenediamine, diethylenetriamine, triethylenetetraamine, tetraethylenepentamine, and mixtures thereof, the hydroxy-containing thickener and borated mercaptan, amine aldehyde condensation product being present in sufficient quantities to effect an increase in the dropping point of said grease.

29. The composition of claim 28 wherein the amine is a polyethylene amine.

* * * * *